United States Patent [19]

Cardwell

[11] Patent Number: 4,932,947

[45] Date of Patent: Jun. 12, 1990

[54] SYRINGE APPARATUS

[76] Inventor: Dieter W. Cardwell, 4710 Forestmanor Dr., Winston-Salem, N.C. 27103

[21] Appl. No.: 312,724

[22] Filed: Feb. 17, 1989

[51] Int. Cl.⁵ ............................................. A61M 5/32
[52] U.S. Cl. ..................................... 604/198; 604/263
[58] Field of Search ............... 604/198, 263, 187, 192, 604/220, 229

[56] References Cited

U.S. PATENT DOCUMENTS

| | | | |
|---|---|---|---|
| 2,876,770 | 3/1959 | White | 128/215 |
| 3,314,380 | 5/1964 | Armao | 128/215 |
| 4,258,713 | 3/1981 | Wardlaw | 128/218 |
| 4,507,118 | 3/1985 | Dent | 604/198 |
| 4,542,749 | 9/1985 | Caselgrandi et al. | 604/198 X |
| 4,664,654 | 5/1987 | Strauss | 604/198 |
| 4,725,267 | 2/1988 | Vaillancourt | 604/198 |
| 4,747,837 | 5/1988 | Hauck | 604/198 |
| 4,767,413 | 8/1988 | Haber et al. | 604/198 |
| 4,787,891 | 11/1988 | Levin et al. | 604/187 X |
| 4,820,275 | 4/1989 | Haber et al. | 604/198 |

Primary Examiner—John D. Yasko

[57] ABSTRACT

Disposable syringe apparatus is provided having a fluid cylinder and needle which is automatically retracted into a protective sleeve in the event of a release of the plunger or in the event the apparatus is accidentally dropped. The syringe apparatus is formed from an inexpensive transparent plastic and may be used for both extractions or injections as needed. A resilient member is positioned exteriorly of the fluid cylinder for ease in assembly and maintenance and acts as a means to attach the fluid cylinder to the protective sleeve.

11 Claims, 3 Drawing Sheets

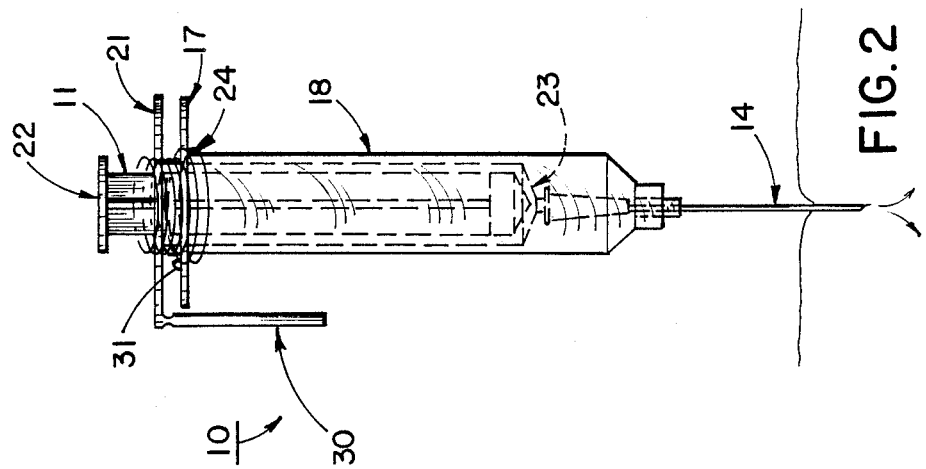
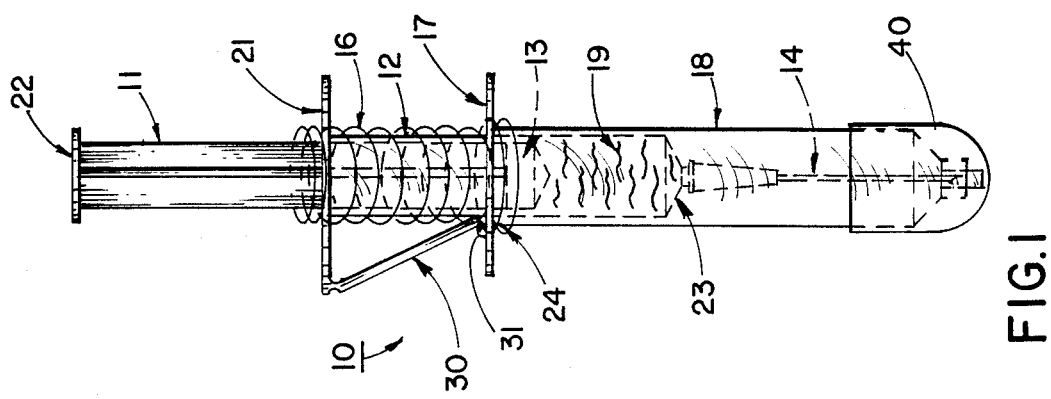

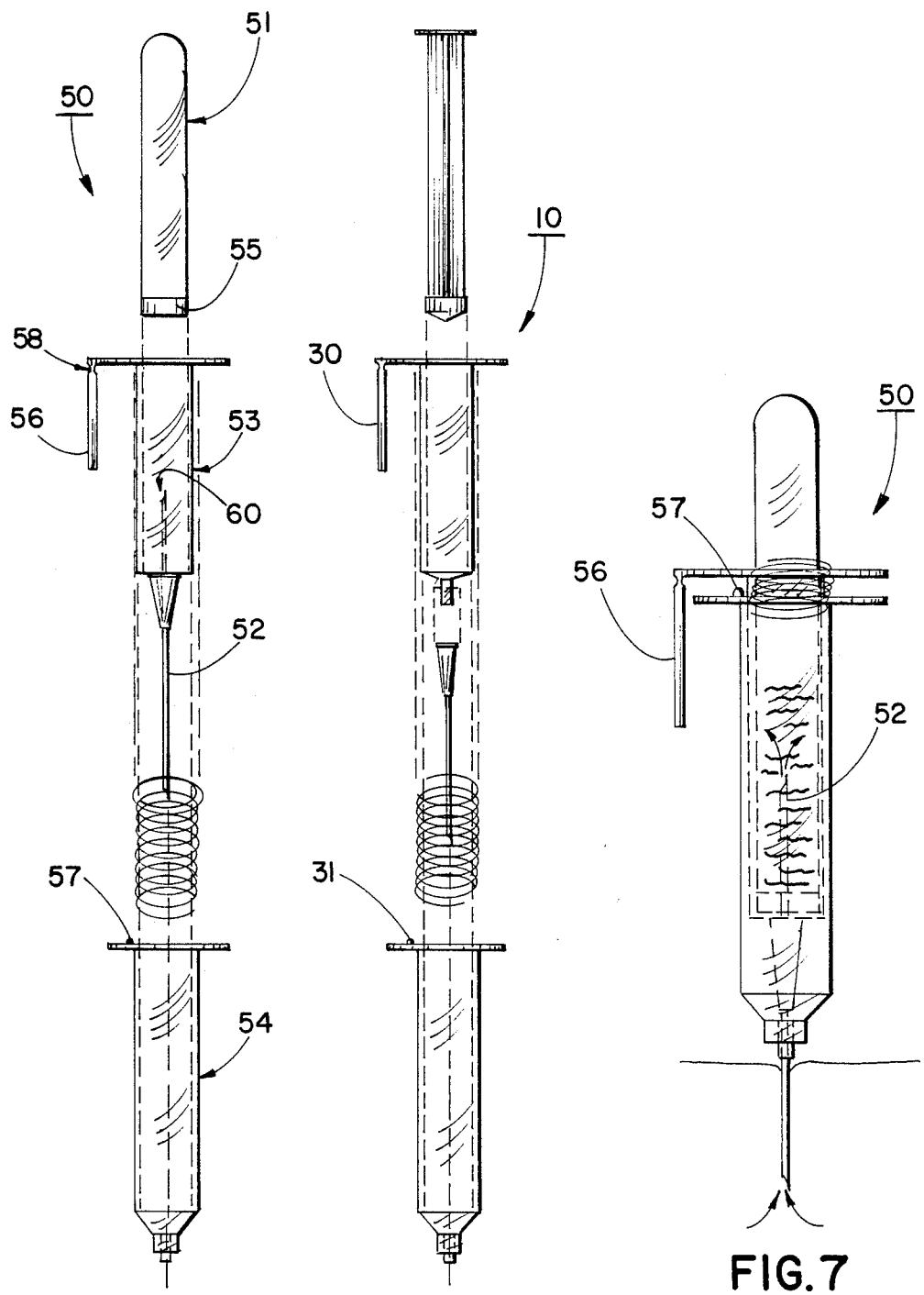

4,932,947

SYRINGE APPARATUS

BACKGROUND OF THE INVENTION

1. Field Of The Invention

The present invention pertains to hypodermic needles and particularly to hypodermic needles used by medical personnel which include sheaths to protect the personnel from accidental punctures with the needle.

2. Description Of The Prior Art
And Objectives Of The Invention

With the increasing spread of contagious diseases such as hepatitis and AIDS, a greater concern has developed by medical personnel over accidental needle puncturing which occasionally occurs during patient injection and extractions. Various types of shielded needle syringes have been constructed in the past such as set forth in U.S. Pat. No. 2,876,770 and U.S. Pat. No. 4,767,413. Such prior art devices are relatively complex in structure and are not intended as inexpensive, disposable instruments. Also, in most prior art retractable needle syringes, the means for retracting the needle, whether it be a coil spring or otherwise, is concealed inside the shield therefore increasing the inconvenience and time required for maintenance in the event the spring malfunctions.

Hence, with the aforesaid and other problems and disadvantages encountered with prior art syringes, the present invention was conceived and one of its objectives is to provide a syringe having a sleeve which will automatically shield the needle when not in use or if the syringe is accidentally dropped.

It is still another objective of the present invention to provide a syringe apparatus which includes a cylindrical transparent fluid container and a transparent sleeve which receives the fluid container whereby the amount of fluid can be easily, visually monitored.

It is yet another objective of the present invention to provide a syringe apparatus which is disposable and relatively easy to assemble.

It is another objective of the present invention to provide a vacuum container collection syringe having removable collection tubes utilizing a double needle.

Another objective of the present invention is to provide a syringe apparatus which is inexpensive to purchase and which can be used to either extract or inject fluids as needed.

It is yet still another objective of the present invention to provide a syringe apparatus having a retractable needle whereby the means for retracting said needle is exposed and exteriorly positioned on the fluid container.

Various other objectives and advantages of the present invention will become apparent to those skilled in the art as a more detailed presentation of the invention is described below.

SUMMARY OF THE INVENTION

The aforesaid and other objectives are realized by providing a syringe apparatus having a cylindrical fluid container resiliently attached to a cylindrical sleeve. The resilient member automatically retracts the fluid cylinder and hypodermic needle attached thereto in the event the apparatus is inadvertently dropped. A safety stop prevents exposure of the needle if the syringe plunger cap is inadvertenly struck as it prevents the fluid cylinder from penetrating sufficiently into the sleeve to expose the needle. The device is formed from an inexpensive synthetic polymer and is therefore disposable, preventing the time consuming necessity of autoclaving or other sterilizing procedures. The resilient member or spring which is exposed allows operating malfunctions to be easily remedied and the device can be assembled and disassembled in a quick and efficient manner.

BRIEF DESCRIPTION OF THE DRAWINGS

FIG. 1 demonstrates a first embodiment of the apparatus of the invention with the fluid cylinder full and the plunger extended therefrom with a safety cap attached;

FIG. 2 shows the invention of FIG. 1 during tissue penetration with the plunger in fully depressed posture with the spring compressed;

FIG. 5 depicts an exploded view of the various components of the syringe apparatus of FIG. 1;

FIG. 6 pictures an exploded embodiment of the invention with a removable vacuum collection tube and double needle; and FIG. 7 shows the embodiment as seen in FIG. 6 with the needle drawing fluid such as blood.

DESCRIPTION OF THE PREFERRED EMBODIMENT

The preferred form of the syringe apparatus is shown in FIGS. 1–5 and includes a fluid cylinder which is resiliently mounted in a transparent sleeve. The sleeve includes a pair of ears which assist the gripping of the apparatus and the spring axially retracts the needle to a position inside the sleeve if the plunger and fluid cylinder are released, or if the apparatus is accidentally dropped. A safety stop is hingedly positioned on the fluid container to prevent the needle from accidentally becoming exposed if the plunger is accidentally depressed or otherwise. The spring is positioned exteriorly of the fluid cylinder and allows simplicity in assembly and disassembly as needed. The plunger which is positioned to be tightly in the fluid cylinder provides for better extraction and injection by the apparatus which is formed from a lightweight inexpensive synthetic polymer for one-time use and disposal purposes.

DETAILED DESCRIPTION OF THE DRAWINGS

AND OPERATION OF THE INVENTION

Figure 4:
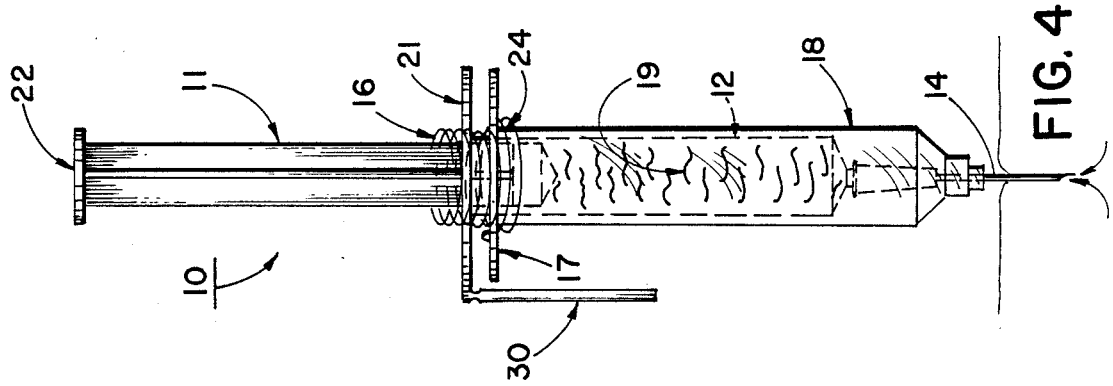
FIG. 4 illustrates the apparatus of FIG. 1 with the needle penetrating tissue, the spring compressed and the plunger in a withdrawn posture such as during fluid extraction.

Turning now to the drawings, for a more detailed description of the invention and its method of operation, syringe apparatus 10 as shown in FIG. 1 includes a plunger 11 which is moveably fitted within fluid cylinder 12. Plunger 11 includes a seal 13 which fits tightly against the inside walls of fluid cylinder 12. Plunger 11, due to the tight fit provided by seal 13 can therefore be used for injection or extraction purposes. Hypodermic needle 14 is attached to cylinder 12 by engaging with nib 15 of fluid cylinder 12 (FIG. 5). As also seen in FIG. 5, fluid cylinder 12 is formed from an inexpensive, substantially transparent synthetic polymer and resilient member 16 consists of a stainless steel coil spring. As further seen in FIGS. 1 and 3, relaxed resilient member 16 is positioned exteriorly of fluid cylinder 12 allowing for easy assembly, maintenance and disassembly of syringe apparatus 10 and resilient member 16 acts as a means to attach cylinder 12 to sleeve 18. In FIG. 1, resilient member 16 attaches to sleeve ears 17 positioned at the proximal end of sleeve 18. Sleeve 18 is also formed from a transparent synthetic polymer such as polyethylene or other inexpensive suitable plastic materials. In FIGS. 1 and 4, fluid 19 which may be an injectable solution or an extractable liquid such as blood can be seen through transparent sleeve 18 and transparent fluid cylinder 12. Sleeve 18 includes a needle aperture 20 through which hypodermic needle 14 passes. During use, resilient member 16 is shown in its normal or relaxed posture in FIG. 1 whereby, by putting finger pressure on cylinder ears 21 cylinder 12 can be substantially directed into sleeve 18 with resilient member 16 compressed as shown in FIG. 2. Blood or other liquids can be drawn through needle 14 as shown in FIG. 4 by applying finger pressure to cylinder ears 21 while withdrawing plunger 11.

Figure 3:
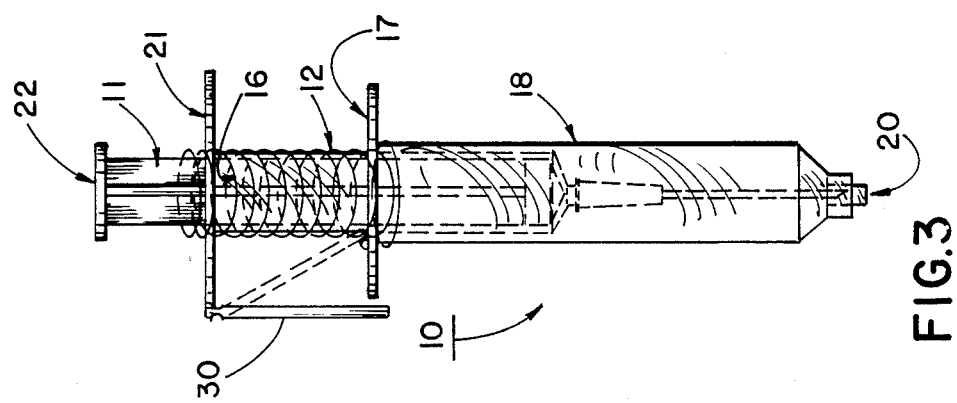
FIG. 3 demonstrates the plunger of the syringe apparatus of FIG. 1 with the plunger fully depressed in the fluid container but with the needle in a fully retracted posture and the fluid container in a locked configuration to prevent needle exposure.

In the event syringe apparatus 10 is accidentally dropped during use with resilient member 16 compressed, resilient member 16 urges fluid container 12 upwardly, out of sleeve 18 as shown in FIG. 3 whereby needle 14 is automatically withdrawn and retracts into sleeve 18 upon relaxation of said resilient member 16, preventing accidental punctures or the like to personnel by needle 14. Also, safety stop 30 which may be a sufficiently sized planar rigid plastic or metal member is hingedly affixed to cylinder ears 21. Safety stop 30 can be moved to the side as seen in FIGS. 2 and 4 when syringe 10 is being used but if accidentally dropped or if plunger cap 22 were accidentally hit, safety stop 30 can be positioned to act as a means to prevent exposure of needle 14, as seen in FIG. 3 as stop 30 "locks" behind ridge 31 located on ears 17. Another safety feature is seen in FIG. 1 whereby syringe cap 40 fits over the end of sleeve 18. Cap 40 can be slid from sleeve 18 prior to use of syringe 10. Fluid cylinder 12 and plunger 11 can be used to inject fluids as shown in FIG. 2 or can be used to extract fluids as shown in FIG. 4. With downward pressure applied to plunger cap 22 fluid cylinder 12 is initially depressed into sleeve 18 until cylinder ears 21 contact compressed spring 16 and sleeve ears 17 (on the proximal end 24 of sleeve 18) as shown in FIG. 2. With continued pressure applied to plunger cap 22, plunger 11 will reach the distal end 23 of fluid cylinder 12 as shown in FIG. 2. Seal 13 is tightly engaged with the inner cylinder walls of cylinder 12 and as would be understood, initial pressure applied to plunger 11 will cause resilient member 16 to compress as fluid cylinder 12 penetrates into sleeve 18. With additional pressure applied, plunger 11 is directed into cylinder 12 as for example, during an injection.

Another embodiment of the invention is shown in FIG. 6 whereby syringe apparatus 50 includes a vacuum container collection tube 51. Needle 52 is permanently affixed to tube holder 53 which slides into sleeve 54. Tube holder 53 acts as a receptacle for collection tube 51 in this embodiment. Conventional collection tube 51 is formed from glass or other rigid, transparent materials and includes plug 55 which is penetrable by double pointed needle 52. Tube holder 53 includes safety stop 56, which as earlier explained serves as a means to prevent the accidental puncturing by needle 52 when positioned over ridge 57. Safety stop 56 is hingedly joined to tube holder 53 by pivot joint 58 as shown also in FIG. 6.

In use, needle 52 is extended from sleeve 54 into a human arm or otherwise to draw blood by depressing holder ears 58 to therefore compress spring member 59. Vacuum collector tube 51 is then urged downward by finger pressure, where needle point 60 penetrates plug 55. The vacuum within collection tube 51 then draws blood through needle 52 into collection tube 51. Once collection tube 51 is filled it can be replaced with another collection tube, while leaving needle 52 embedded within the arm as seen in FIG. 7. When the blood extraction process is complete, ears 58 are released and spring member 59 returns tube holder 53 to its raised position with needle 52 within sleeve 54 preventng an accidental puncture. Spring member 59 threfore acts as means to exteriorly resiliently attach tube holder 53 to sleeve 54. Safety stop 56 can then be positioned over ridge 57 to prevent accidental exposure of needle 52.

The illustrations and examples provided herein are for explanatory purposes and are not intended to limit the scope of the appended claims.

I claim:

1. Syringe apparatus comprising: a fluid cylinder, a plunger, said plunger moveably positioned within said cylinder, a hypodermic needle, said needle affixed to said cylinder, a cylinder ear, said ear attached to said cylinder, a cylinder stop, said stop pivotally attached to said cylinder ear, a cylinder sleeve, means to resiliently attach said cylinder to said sleeve, and said resilient means positioned exteriorly of said sleeve for retracting said needle into said sleeve.

2. Syringe apparatus as claimed in claim 1 wherein said resilient means comprises a coil spring.

3. Syringe apparatus as claimed in claim 1 wherein said fluid cylinder is transparent.

4. Syringe apparatus as claimed in claim 1 wherein said cylinder sleeve is transparent.

5. Syringe apparatus as claimed in claim 1 and including a sleeve ear, said sleeve ear positioned at the proximal end of said sleeve.

6. Syringe apparatus as claimed in claim 5 and including a means to lock said stop, said locking means attached to said sleeve ear.

7. Syringe apparatus as claimed in claim 1 wherein said sleeve defines a needle aperture at the distal end thereof.

8. Syringe apparatus comprising: a transparent fluid cylinder, a plunger, said plunger moveably positioned within said cylinder, a hypodermic needle, said hypodermic needle attached to said fluid cylinder, a transparent cylinder sleeve, resilient means for attaching cylinder to said sleeve, a cylinder ear, said ear attached to the proximal end of said fluid cylinder, a stop, said stop pivotally joined to said cylinder ear, a pair of sleeve ears, said ears positioned on the proximal end of said sleeve, means to lock said stop, said locking means attached to one of said sleeve ears, said resilient means affixed to said ears and exteriorly of said fluid cylinder whereby said resilient means can be compressed and thereafter can withdraw said cylinder and attached needle into said sleeve as said resilient means relaxes.

9. Syringe apparatus as claimed in claim 8 wherein said stop is affixed to the terminal end of said cylinder ear, said stop to prevent accidental compression of said resilient means.

10. Syringe apparatus as claimed in claim 9 wherein said stop means is hingedly affixed to the terminal end of said cylinder ear.

11. Syringe apparatus as claimed in claim 1 wherein said fluid cylinder comprises a collection tube receptacle.

* * * * *